United States Patent
Aerts

(10) Patent No.: US 8,542,017 B2
(45) Date of Patent: Sep. 24, 2013

(54) SYSTEM AND METHOD FOR MEASURING THE SHAPE OF AN ORGAN OF A PATIENT USING A MAGNETIC INDUCTION RADIO SENSOR INTEGRATED IN A STRETCHABLE STRAP

(75) Inventor: Steven Aerts, Oud-Heverlee (BE)

(73) Assignee: NXP B.V., Eindhoven (NL)

(*) Notice: Subject to any disclaimer, the term of this patent is extended or adjusted under 35 U.S.C. 154(b) by 733 days.

(21) Appl. No.: 12/643,985

(22) Filed: Dec. 21, 2009

(65) Prior Publication Data

US 2011/0148409 A1 Jun. 23, 2011

(51) Int. Cl.
*G01R 33/36* (2006.01)
*A61B 5/055* (2006.01)

(52) U.S. Cl.
USPC ........... 324/322; 324/318; 324/309; 600/421; 600/411; 600/425

(58) Field of Classification Search
USPC ........... 324/300–322, 207.17; 600/407–435, 600/534, 595; 343/703; 382/128–131; 73/149; 702/150; 323/330; 12/17 R
See application file for complete search history.

(56) References Cited

U.S. PATENT DOCUMENTS

| | | | | |
|---|---|---|---|---|
| 2,869,074 A * | 1/1959 | Clapp | | 324/234 |
| 2,919,436 A * | 12/1959 | Forman | | 340/870.13 |
| 3,195,540 A * | 7/1965 | Waller | | 607/33 |
| 3,296,533 A * | 1/1967 | Karpinsky | | 343/703 |
| 3,402,346 A * | 9/1968 | Baker | | 324/322 |
| 3,506,993 A * | 4/1970 | Barker et al. | | 12/17 R |
| 3,519,918 A * | 7/1970 | Bruck | | 323/330 |
| 3,560,983 A * | 2/1971 | Willie et al. | | 343/744 |
| 4,308,872 A | 1/1982 | Watson et al. | | |
| 4,737,718 A * | 4/1988 | Kemner et al. | | 324/322 |
| 6,374,667 B1 * | 4/2002 | Eriksen et al. | | 73/149 |
| 6,504,361 B1 * | 1/2003 | Gleixner | | 324/207.17 |
| 6,945,941 B2 * | 9/2005 | Eriksen et al. | | 600/534 |
| 7,390,307 B2 * | 6/2008 | Eriksen et al. | | 600/595 |
| 7,514,926 B2 * | 4/2009 | Adriany et al. | | 324/318 |
| 7,541,810 B2 * | 6/2009 | Yoshida et al. | | 324/318 |
| 2002/0123701 A1 * | 9/2002 | Eriksen et al. | | 600/595 |
| 2003/0135127 A1 | 7/2003 | Sackner et al. | | |
| 2004/0133117 A1 * | 7/2004 | Eriksen et al. | | 600/534 |
| 2007/0108980 A1 * | 5/2007 | Adriany et al. | | 324/318 |
| 2007/0177414 A1 | 8/2007 | Funato et al. | | |
| 2008/0270067 A1 * | 10/2008 | Eriksen et al. | | 702/150 |
| 2011/0018539 A1 * | 1/2011 | Viswanathan | | 324/318 |
| 2011/0043209 A1 * | 2/2011 | Zhu | | 324/322 |
| 2011/0148409 A1 * | 6/2011 | Aerts | | 324/307 |

FOREIGN PATENT DOCUMENTS

| | | |
|---|---|---|
| GB | 2108676 A | 5/1983 |
| JP | 2004-150954 A | 5/2004 |
| WO | 2009156879 A1 | 12/2009 |

\* cited by examiner

*Primary Examiner* — Melissa Koval
*Assistant Examiner* — Tiffany Fetzner

(57) ABSTRACT

A system and method for measuring the shape of an object using a magnetic induction radio sensor involves at least partially enclosing the object with a magnetic loop antenna of the magnetic induction radio sensor, where the inductance of the magnetic loop antenna depends on the shape of the object, and providing a particular capacitance at an antenna matching circuit coupled to the magnetic loop antenna in response to the inductance of the magnetic loop antenna such that the magnetic loop antenna and the antenna matching circuit form a resonant circuit and the resonant circuit has a fixed resonant frequency, where the particular capacitance is used to measure the shape of the object.

18 Claims, 8 Drawing Sheets

SYSTEM AND METHOD FOR MEASURING THE SHAPE OF AN ORGAN OF A PATIENT USING A MAGNETIC INDUCTION RADIO SENSOR INTEGRATED IN A STRETCHABLE STRAP

Embodiments of the invention relate generally to electronics systems and, more particularly, to a system and method for measuring the shape of an object.

Measuring the shape of an object is important to various applications. For example, monitoring the activity of an organ of a patient by measuring the body area near the organ as that body area changes over time due to the organ is vital to the health care of the patient.

Conventionally, a sensor that measures the shape of an object is connected to an external device using wires to transmit measurement data for processing and displaying. However, installing wires to connect the sensor and the external device reduces the mobility of the measured object. For patient monitoring, using wires to connect the sensor and the external device will also decrease the comfort level of the patient. Therefore, there is a need to provide a system and method for measuring the shape of an object that can improve both the mobility and the comfort level of the measured object.

A system and method for measuring the shape of an object using a magnetic induction radio sensor involves at least partially enclosing the object with a magnetic loop antenna of the magnetic induction radio sensor, where the inductance of the magnetic loop antenna depends on the shape of the object, and providing a particular capacitance at an antenna matching circuit coupled to the magnetic loop antenna in response to the inductance of the magnetic loop antenna such that the magnetic loop antenna and the antenna matching circuit form a resonant circuit and the resonant circuit has a fixed resonant frequency, where the particular capacitance is used to measure the shape of the object. By measuring the shape of the object using the magnetic induction radio sensor, both the mobility and the comfort level of the measured object are improved.

In an embodiment, a magnetic induction radio sensor for measuring the shape of an object includes a magnetic loop antenna, an antenna matching circuit and a measuring unit. The magnetic loop antenna is configured to at least partially enclose the object, where the inductance of the magnetic loop antenna depends on the shape of the object. The antenna matching circuit is coupled to the magnetic loop antenna, where the antenna matching circuit includes an adjustable capacitance module configured to provide a particular capacitance such that the magnetic loop antenna and the antenna matching circuit form a resonant circuit and the resonant circuit has a fixed resonant frequency. The measuring unit is configured to generate a measurement value using the particular capacitance of the adjustable capacitance module, where the measurement value represents a measurement of the shape of the object.

In an embodiment, a method for measuring the shape of an object using a magnetic induction radio sensor involves at least partially enclosing the object with a magnetic loop antenna of the magnetic induction radio sensor, where the inductance of the magnetic loop antenna depends on the shape of the object, providing a particular capacitance at an antenna matching circuit coupled to the magnetic loop antenna such that the magnetic loop antenna and the antenna matching circuit form a resonant circuit and the resonant circuit has a fixed resonant frequency, and generating a measurement value using the particular capacitance, where the measurement value represents a measurement of the shape of the object.

In an embodiment, a magnetic induction radio system for measuring the shape of an object includes a magnetic induction radio sensor and a remote device. The magnetic induction radio sensor includes a magnetic loop antenna, an antenna matching circuit, a measuring unit and a transmitter. The magnetic loop antenna is configured to at least partially enclose the object, where the inductance of the magnetic loop antenna depends on the shape of the object. The antenna matching circuit is coupled to the magnetic loop antenna, where the antenna matching circuit includes an adjustable capacitance module configured to provide a particular capacitance such that the magnetic loop antenna and the antenna matching circuit form a resonant circuit and the resonant circuit has a fixed resonant frequency. The measuring unit is configured to generate a measurement value using the particular capacitance of the adjustable capacitance module, where the measurement value represents a measurement of the shape of the object. The transmitter is configured to transmit the generated measurement value using the magnetic loop antenna. The remote device is configured to receive the transmitted measurement value from the transmitter of the magnetic induction radio sensor.

Other aspects and advantages of embodiments of the present invention will become apparent from the following detailed description, taken in conjunction with the accompanying drawings, depicted by way of example of the principles of the invention.

Throughout the description, similar reference numbers may be used to identify similar elements.

Figure 1:
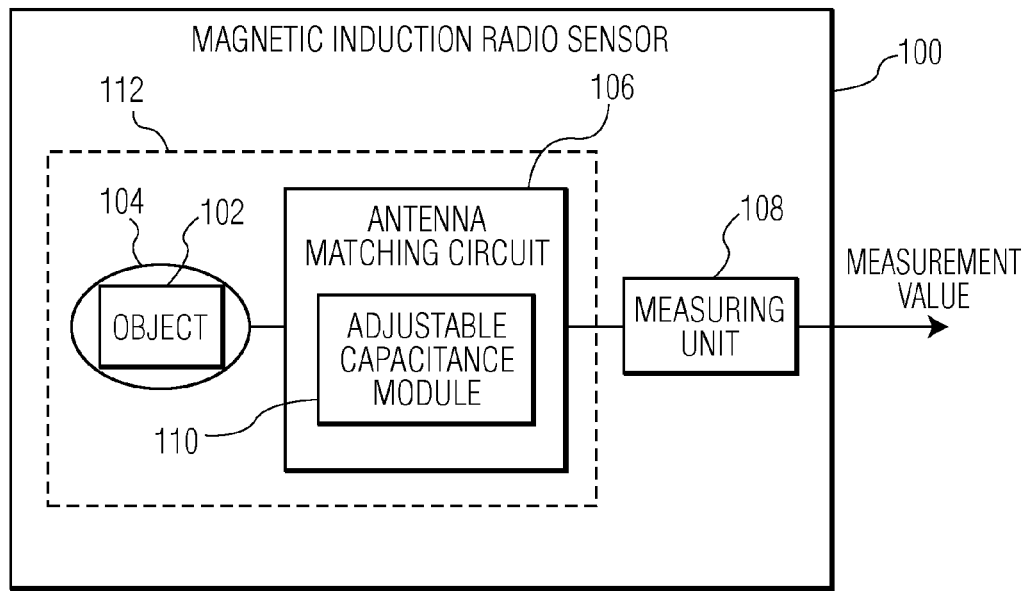
FIG. 1 shows a schematic block diagram of a magnetic induction radio sensor in accordance with an embodiment of the invention.

FIG. 1 shows a schematic block diagram of a magnetic induction radio sensor 100 in accordance with an embodiment of the invention. The magnetic induction radio sensor is configured to measure the shape of an object 102 and wirelessly transmit the measurement using magnetic induction. Magnetic induction is well-known in the art and is briefly described as follows. An electrical current that goes through a wire such as a loop antenna produces an electromagnetic field, which includes a magnetic field around the wire and an electric field that radiates away from the wire. For far field where the distance is far larger than the respective wavelength, the radiation effect of the electric field dominates. However, for near field where the distance is far smaller than the respective wavelength, the induction effect of the magnetic field dominates. When a second wire such as a loop antenna is introduced within the magnetic field, the magnetic flux passes through a surface of the second wire. The magnetic flux variations induce electromotive force (EMF) and the induced EMF generates a current.

Compared to a radio frequency (RF) sensor, the magnetic induction radio sensor 100 has a number of advantages. Firstly, the magnetic induction radio sensor is more power-efficient at short distance and can achieve a longer autonomy or requires a smaller battery than an RF sensor. Secondly, the magnetic induction radio sensor goes through human tissue with low degradation of signal strength while RF signals are attenuated by the body and depend on line of sight or reflection for signal propagation. Additionally, RF signals are easily absorbed by human tissue and as a result can raise health issues for medical applications. Thirdly, unlike an RF sensor, the magnetic induction radio sensor does not need a crystal to keep spectrum within regulated bandwidth boundaries. As a result, the magnetic induction radio sensor can be easily integrated into a single chip. Fourthly, the strength of the magnetic induction signal degrades steeply as a function of distance. As a result, interference level of the magnetic induction signal is reduced and the robustness of the magnetic induction signal is increased. Additionally, to intercept the magnetic induction signal, an eavesdropper needs to be at a close physical range of the magnetic induction signal, and as a result, the security of the magnetic induction signal is improved. Furthermore, the identification of the magnetic induction radio sensor is more intuitive and reliable than an RF sensor. Fifthly, the cost of manufacturing the magnetic induction radio sensor is lower than the cost of manufacturing an RF sensor. For example, testing of the magnetic induction radio sensor during manufacturing is simpler than an RF sensor because of smaller sealed radio area. Additionally, compliance with regulations such as Federal Communications Commission (FCC) for the magnetic induction radio sensor is easier than a conventional RF sensor because the transmit power of the magnetic induction radio sensor is typically far below the set limit. Sixthly, the magnetic induction radio sensor can be charged using near-field magnetic induction. Additionally, the magnetic induction radio sensor can operate without a battery using direct inductive power that is received by its antenna. For example, inductive and wireless charging can be used for sealed wearable magnetic induction radio sensor through its magnetic antenna coil. Seventhly, when the magnetic induction radio sensor is used to measure the shape of an object, only a minimal addition to the embedded software is required while no additional hardware components are needed.

In the illustrated embodiment of FIG. 1, the magnetic induction radio sensor 100 includes a magnetic loop antenna 104, an antenna matching circuit 106 and a measuring unit 108. The antenna matching circuit and the measuring unit of the magnetic induction radio sensor can be implemented in a single integrated circuit (IC) chip to reduce manufacturing cost and the size of the magnetic induction radio sensor. The magnetic loop antenna of the magnetic induction radio sensor is configured to at least partially enclose the object 102. In an example, the object that is at least partially enclosed by the magnetic loop antenna constitutes the core of the magnetic loop antenna. Although the magnetic loop antenna is shown in FIG. 1 as fully enclosing the object, the magnetic loop antenna may only partially enclose the object in some embodiments. For example, the magnetic loop antenna is mounted on a stretchable substrate material and fixed to anchor points of one or more objects, where movement of the anchor points causes the deformation of the stretchable substrate material and the magnetic loop antenna and the change of the inductance of the magnetic loop. The inductance of the magnetic loop antenna depends on the shape of the object. Thus, the inductance of the magnetic loop antenna changes as the shape of the object changes. In some embodiments, the inductance of the magnetic loop antenna is approximately proportional to the area of the object that is enclosed by the magnetic loop antenna.

In some embodiments, the magnetic loop antenna 104 is a stretchable magnetic loop antenna, which has one or more turns, that at least partially encloses the object 102. The magnetic loop antenna deforms and changes its inductance as a result of expansion and/or contraction of the object. For example, the magnetic loop antenna includes a conductor that is mounted on a stretchable substrate. The conductor may be a single-turn or a multi-turn conducting wire such as a copper track in a sinusoidal shape, a spiral shape or a meandering shape. The stretchable substrate may be a woven stretchable material or a non-woven stretchable material made by technology developed in EU subsidized project STretchable ELectronics for Large Area applications (STELLA) (IST-028026). The conductor and the stretchable substrate may at least partially enclose the object such that any cross-sectional or volumetric changes of the object are reflected in changes of the inductance of the magnetic loop antenna. For example, the magnetic loop antenna is mounted on a stretchable substrate material and fixed to anchor points of one or more objects, where movement of the anchor points causes the deformation of the stretchable substrate material and the magnetic loop antenna and the change of the inductance of the magnetic loop. In an example, the inductance of a single-turn magnetic loop antenna can be given by:

$$L = r \cdot \left( \ln\left(\frac{8 \cdot r}{a}\right) - 2 + Y \right) \qquad (1)$$

where L represents the inductance of the single-turn magnetic loop antenna, r represents the loop radius, a represents the wire radius, Y=0 ... ¼, which is decided by the result of skin effect versus uniform current distribution. If the wire radius a is much larger than the skin depth, the skin effect is fully deployed and Y is equal to 0. If the wire radius a is much smaller than the skin depth, the current distributes uniformly and Y is equal to ¼.

Figure 2:
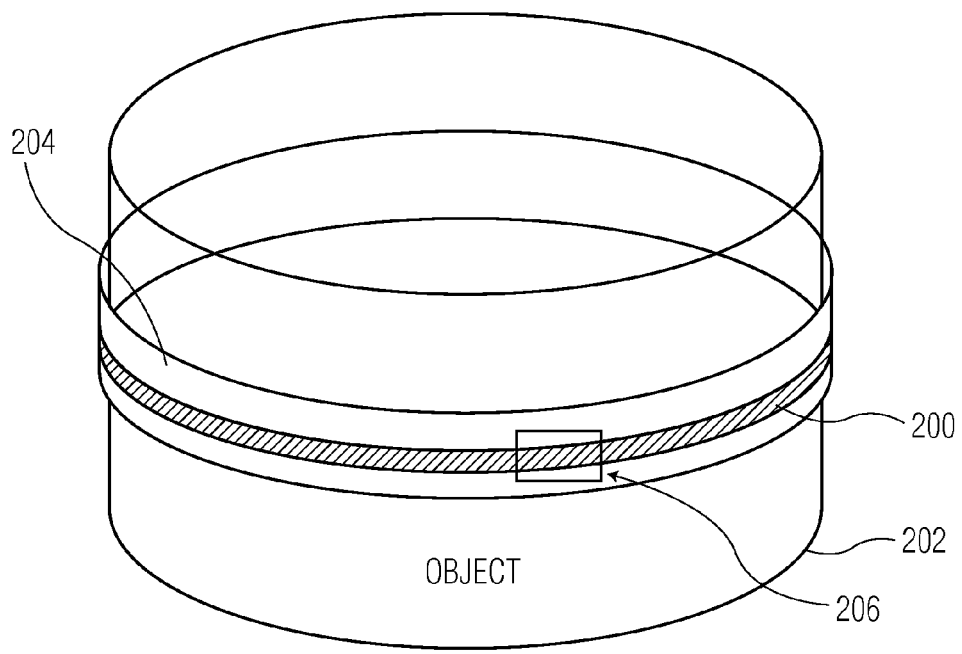
FIG. 2 depicts an exemplary stretchable magnetic loop antenna.

Examples of stretchable magnetic loop antennas are depicted in FIGS. 2-7. FIG. 2 shows an exemplary stretchable magnetic loop antenna 200 that fully encloses an object 202. In the embodiment of FIG. 2, the stretchable magnetic loop antenna is formed on a stretchable substrate 204. As shown in FIG. 2, the object is completely encircled by the stretchable magnetic loop antenna. The magnetic loop antenna deforms and changes its inductance as a result of expansion and/or contraction of the object.

Figure 3:
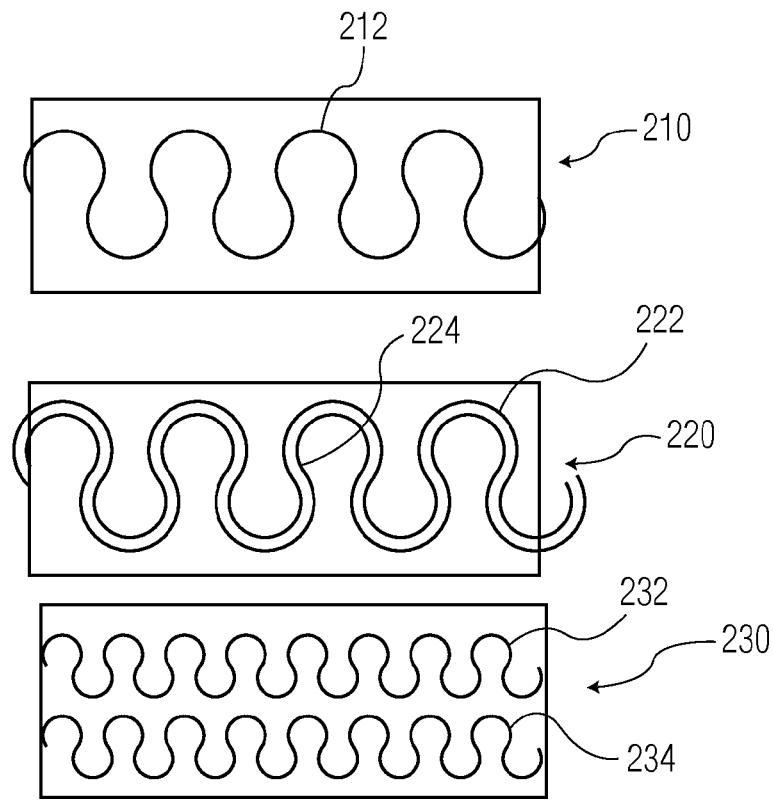
FIG. 3 shows three examples of an antenna section of the stretchable magnetic loop antenna of FIG. 2.

The stretchable magnetic loop antenna 200 may be formed by a single-turn or a multi-turn conducting wire in any suitable shape, such as a sinusoidal shape, a spiral shape or a meandering shape. Three examples of an antenna section 206 of the stretchable magnetic loop antenna are depicted in FIG. 3. As depicted in FIG. 3, a first exemplary antenna section 210 is formed by a single-turn conducting wire 212 having a meandering shape. A second exemplary antenna section 220 is formed by two meandering-shaped single-turn conducting wires 222, 224, where the single-turn conducting wire 224 is located slightly below the single-turn conducting wire 222. A third exemplary antenna section 230 is formed by two meandering-shaped conducting wires 232, 234, where the single-turn conducting wire 234 is located completely below the single-turn conducting wire 232.

Figure 4:
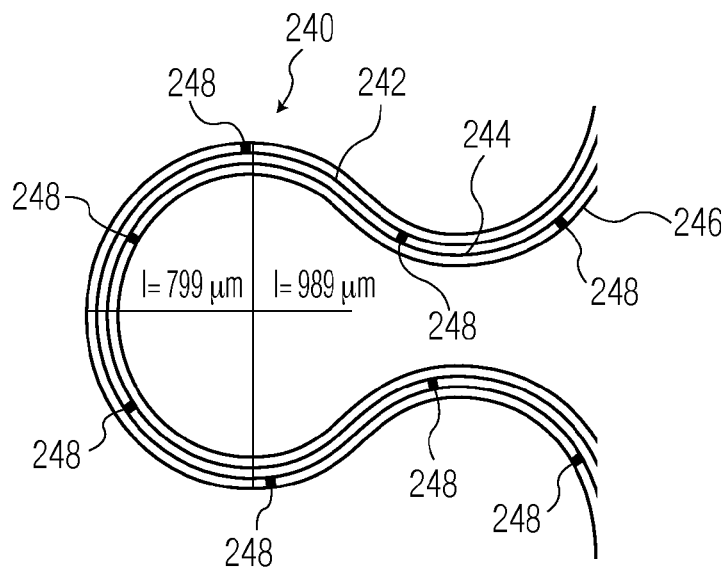
FIG. 4 shows an exemplary meandering conductor track set of the stretchable magnetic loop antenna of FIG. 2.

The stretchable magnetic loop antenna 200 may be made of meandering conductor track sets. An exemplary meandering conductor track set 240 is depicted in FIG. 4. As shown in FIG. 4, the meandering conductor track set includes multiple stretchable copper tracks 242, 244, 246 that are stacked together and are connected by conductor bridges 248. The stacking of the multiple stretchable copper tracks with conductor bridges improves the reliability of the conductivity of the meandering track set. When a crack appears in one of the copper tracks, a conductive path is maintained by a neighbor copper track through the conductor bridges. The meandering shape of the meandering track set enables the stretchability of the copper tracks such that these copper tracks can be used to construct the magnetic loop antenna. For example, interconnecting meandering conductor tracks are embedded in a transparent material that is shaped according to the meandering shape of the conductor tracks to form the magnetic loop antenna.

Figure 5:
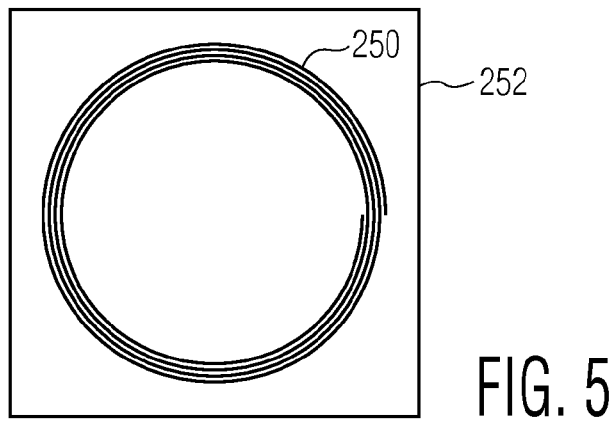
FIG. 5 depicts another exemplary stretchable magnetic loop antenna.
Figure 6:
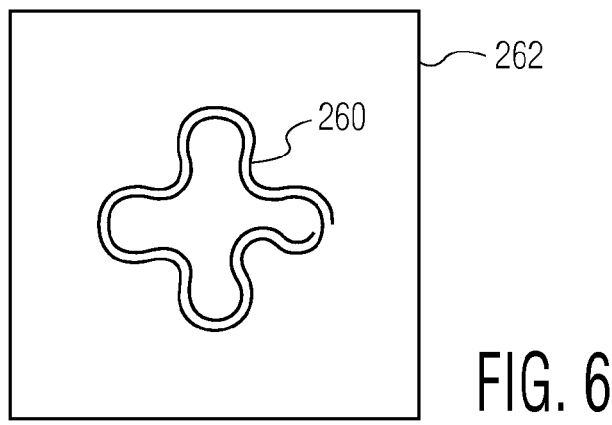
FIG. 6 depicts another exemplary stretchable magnetic loop antenna.

FIG. 5 shows an exemplary stretchable magnetic loop antenna 250 that only partially encloses an object. In the embodiment of FIG. 5, the stretchable magnetic loop antenna is a flat spiral loop antenna formed on a stretchable substrate 252, which can be patched onto the object. FIG. 6 shows another exemplary stretchable magnetic loop antenna 260 that only partially encloses an object. In the embodiment of FIG. 6, the stretchable magnetic loop antenna is a meandering clover shaped loop antenna formed on a stretchable substrate 262, which can be patched onto the object. In the embodiments in FIG. 5 and FIG. 6, the magnetic loop antenna deforms and changes its inductance as a result of movements of the object.

Figure 7:
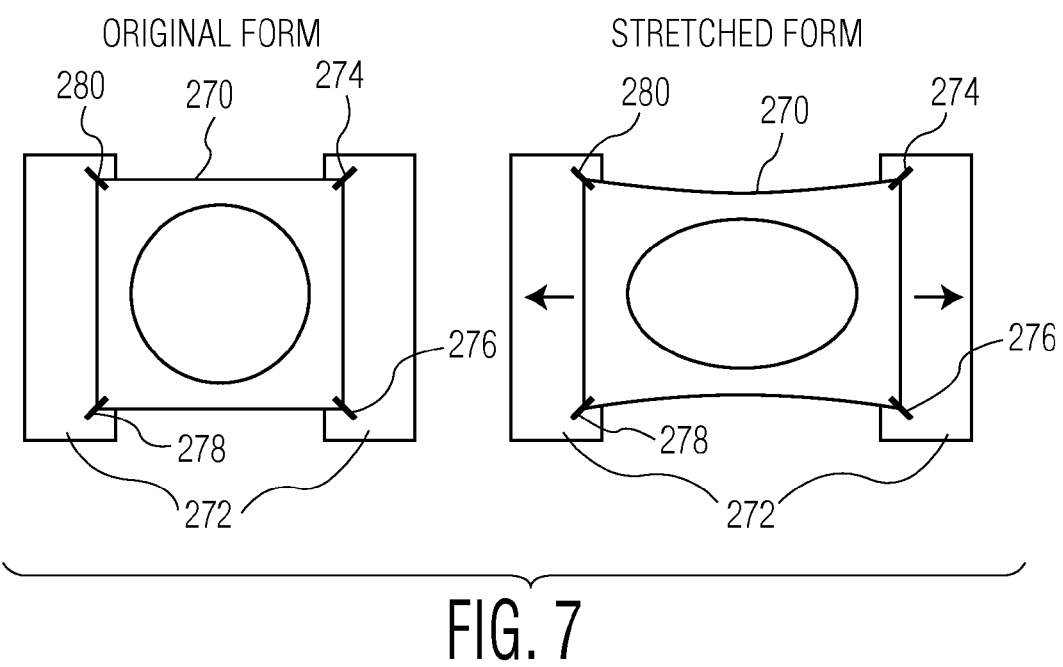
FIG. 7 illustrates the effects on an exemplary stretchable magnetic loop antenna when the loop antenna is stretched.

In some embodiments, a stretchable magnetic loop antenna is fixed to anchor points of one or more objects, where movements of the anchor points cause deformations of the magnetic loop antenna and change the inductance of the magnetic loop. FIG. 7 illustrates the effects on an exemplary stretchable magnetic loop antenna 270 that is fixed to an object 272 when the loop antenna is stretched. In the embodiment of FIG. 7, the stretchable magnetic loop antenna is fixed to the object through four anchor points 274, 276, 278, 280. Before being stretched, the stretchable magnetic loop antenna is in its original form, as shown on the left side of FIG. 7. When stretched, the stretchable magnetic loop antenna changes from its original form to a stretched form, as shown on the right side of FIG. 7. The movement of the anchor points causes the deformation of the stretchable magnetic loop antenna, which results in change of the inductance of the stretchable magnetic loop antenna.

In some embodiments, the object 102 being measured is an organ of a patient and the magnetic loop antenna 104 is integrated in a stretchable strap that at least partially encloses the organ of the patient. In an example, the organ is a lung of the patient and the stretchable strap wraps around the chest and/or abdomen of the patient to measure expansion and/or contraction of the torso of the patient to measure respiration of the patient. In another example, the organ is a limb of the patient and the stretchable strap wraps around the limb of the patient to measure expansion and/or contraction of muscles of the limb. In some embodiments, the stretchable strap includes contact electrodes integrated in the stretchable strap and configured to measure bio-potentials of the patient.

Although the magnetic induction radio sensor 100 is shown in FIG. 1 as including a single magnetic loop antenna 104, the magnetic induction radio sensor may include multiple magnetic loop antennas and an array of switches for selecting the magnetic loop antennas in some embodiments. The magnetic loop antennas at least partially enclose the object around different areas of the object and the inductances of the magnetic loop antennas depend on the shape of the object.

The antenna matching circuit 106 of the magnetic induction radio sensor 100 is coupled to the magnetic loop antenna 104. The antenna matching circuit includes an adjustable capacitance module 110 that is configured to provide a particular capacitance such that the magnetic loop antenna and the antenna matching circuit have a fixed resonant frequency. In other words, the magnetic loop antenna and the antenna matching circuit form a resonant circuit 112 and the resonant circuit has a fixed resonant frequency. In some embodiments, the antenna matching circuit further includes one or more resistors, which may be adjustable. The relationship between the resonant frequency of the resonant circuit, the inductance of the magnetic loop antenna and the capacitance of the adjustable capacitance module can be expressed as:

$$fr = \frac{1}{2 \times \pi \times \sqrt{L \times C}} \quad (2)$$

where $f_r$ represents the resonant frequency of the resonant circuit, L represents the inductance of the magnetic loop antenna and C represents the capacitance of the adjustable capacitance module. As the resonant frequency of the resonant circuit $f_r$ is fixed, the product of L and C is fixed. To maintain the fixed resonant frequency $f_r$, a change in the inductance L will be compensated by a reciprocal change in the capacitance C. Therefore, the instantaneous value of the capacitance C can be used to measure the inductance value L that is dependent on the shape of the enclosed object 102.

Figure 8:
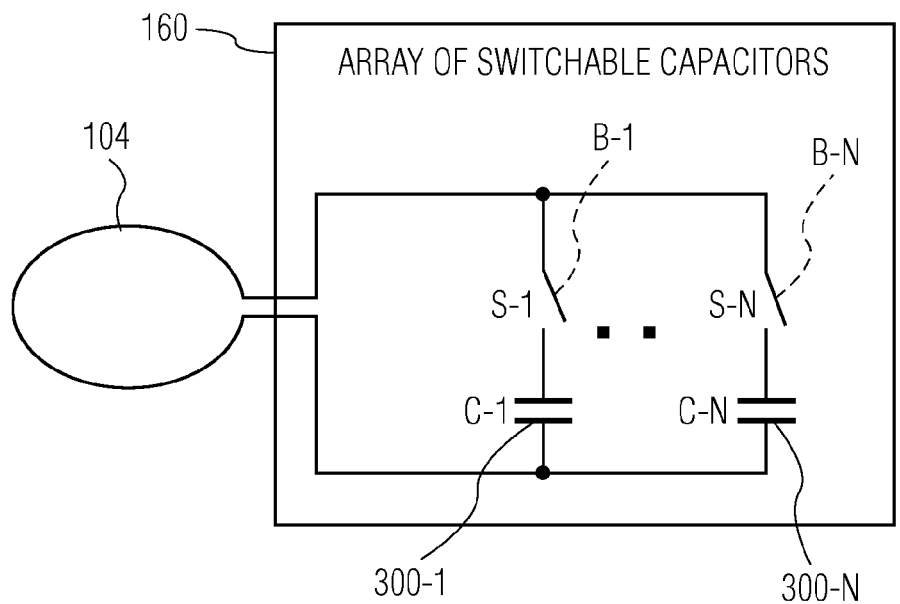
FIG. 8 and FIG. 9 depict two exemplary arrays of switchable capacitors.
Figure 9:
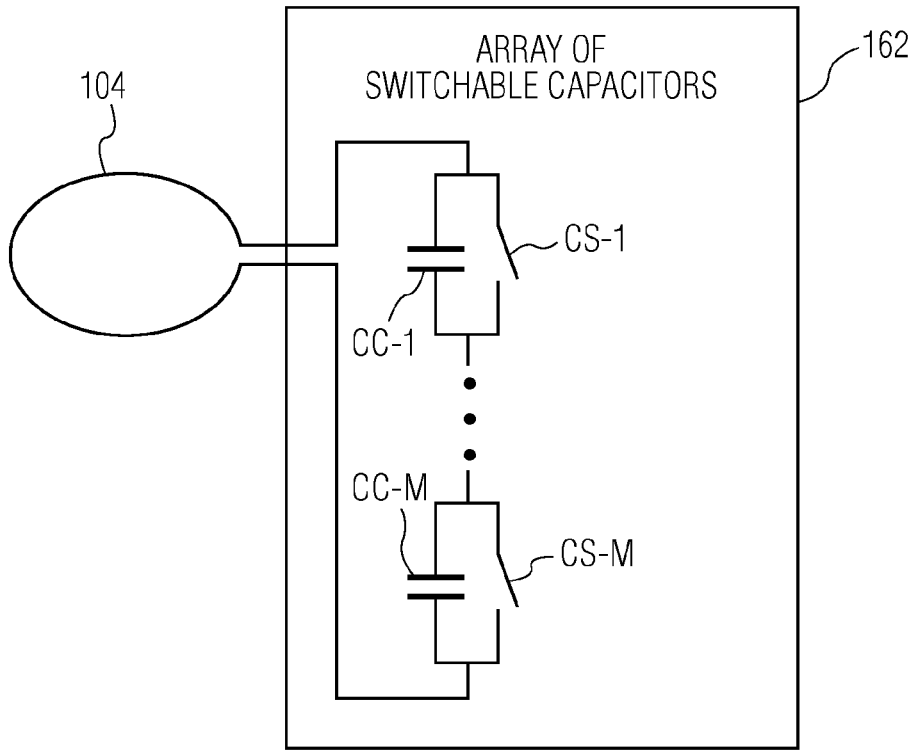

In some embodiments, the adjustable capacitance module 110 includes an array of switchable capacitors to provide the particular capacitance. Compared to a varicap, which is also referred to as a varactor diode or a variable capacitance diode, an array of switchable capacitors can be easily integrated in a Complementary Metal Oxide Semiconductor (CMOS) device and does not require a direct current (DC) voltage biasing. FIG. 8 and FIG. 9 depict two example of the array of switchable capacitors 160, 162.

In some embodiments, the array of switchable capacitors includes capacitor branches that are connected in parallel with the magnetic loop antenna, where each of the capacitor branches includes a switch and a capacitor. As shown in FIG. 8, the array of switchable capacitors 160 includes capacitor branches 300-1 . . . 300-N, where N is an integer that is larger than 1. The capacitor branches 300-1 . . . 300-N are connected in parallel with the magnetic loop antenna 104 and each of the capacitor branches 300-1 . . . 300-N includes a switch and a capacitor. In the embodiment of FIG. 8, the capacitor branch 300-1 includes a switch S-1 and a capacitor C-1 while the capacitor branch 300-N includes a switch S-N and a capacitor C-N. The capacitors C-1 ... C-N are controlled by an N bit control value. In the embodiment of FIG. 8, the capacitor C-1 is controlled by bit B-1 while the capacitor C-N is controlled by bit B-N. In an embodiment, capacitances of the capacitors C-1 ... C-N in the capacitor branches 300-1 ... 300-N have a numeric relationship of factors of two. For example, $$C_1 = \frac{C_p}{2}, \ldots, C_N = \frac{C_p}{2^N}, \quad (3)$$

where $C_1$ represents the capacitance of the capacitor C-1, $C_N$ represents the capacitance of the capacitor C-N, and $C_p$ represents a predefined capacitance, which is the smallest amount by which the capacitance of the array of switchable capacitors can be changed. The overall capacitance of the array of switchable capacitors can be expressed as:

$$C_a = C_p * B_{control} \quad (4)$$

where $C_a$ represents the overall capacitance of the array of switchable capacitors and $B_{control}$ represents the N bit control value B-1 ... B-N. In another embodiment, the capacitances of the capacitors C-1 ... C-N are equal such that $$C_1 =, \ldots, = C_N, \quad (5)$$

where $C_1$ represents the capacitance of the capacitor C-1 and $C_N$ represents the capacitance of the capacitor C-N.

In some embodiments, the array of switchable capacitors includes cascaded capacitors that are connected serially or in parallel with the magnetic loop antenna, where each of the cascaded capacitors is coupled to a switch and has the same capacitance value. As shown in FIG. 9, the array of switchable capacitors 162 includes cascaded capacitors CC-1 ... CC-M, where M is an integer that is larger than 1. The cascaded capacitors CC-1 ... CC-M are connected serially with the magnetic loop antenna 104. Each of the cascaded capacitors CC-1 ... CC-M is connected to a switch. In the embodiment of FIG. 9, the capacitor CC-1 is coupled to a switch CS-1 while the capacitor CC-M is coupled to a switch CS-M.

Turning back to FIG. 1, the measuring unit 108 of the magnetic induction radio sensor 100 is configured to generate a measurement value using the particular capacitance of the adjustable capacitance module, where the measurement value represents a measurement of the shape of the object 102. In an embodiment, the generated measurement value is the particular capacitance value provided by the adjustable capacitance module 110 of the antenna matching circuit 106 such that the resonant circuit 112 has the fixed resonant frequency for the inductance of the magnetic loop antenna 104. The generated measurement value may be transmitted to a remote device (not shown) using the magnetic loop antenna 104 for display and/or processing.

Figure 10:
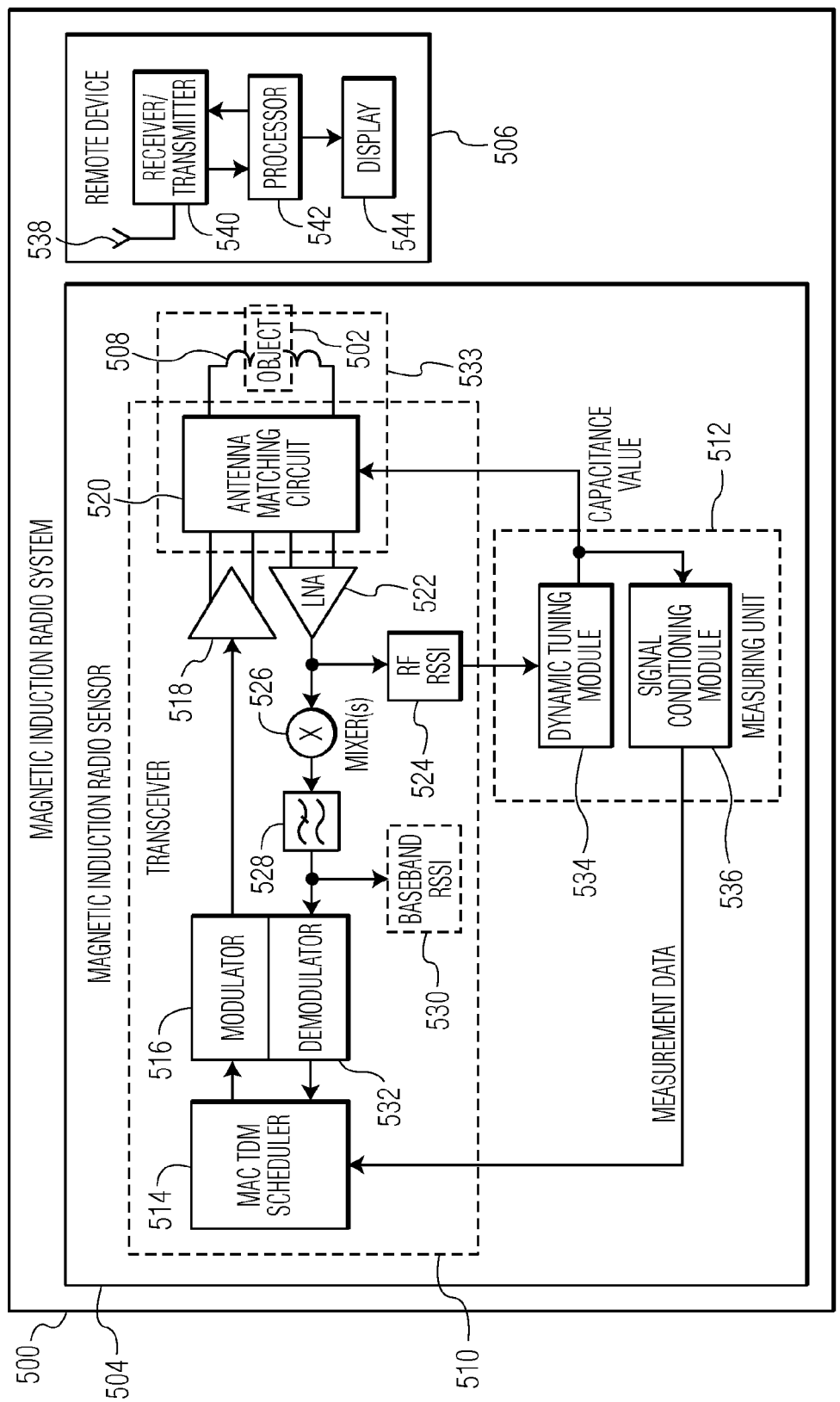
FIG. 10 shows a schematic block diagram of a magnetic induction radio system in accordance with an embodiment of the invention.

FIG. 10 shows a schematic block diagram of a magnetic induction radio system 500 in accordance with an embodiment of the invention. The magnetic induction radio system is configured to measure the shape of an object 502, and thus, can also measure any changes in the shape of the object. As shown in FIG. 10, the magnetic induction radio system includes a magnetic induction radio sensor 504 and a remote device 506. Although the magnetic induction radio system is shown as including one magnetic induction radio sensor and one remote device, the magnetic induction radio system may include more than one magnetic induction radio sensor and/or more than one remote device in some embodiments.

The magnetic induction radio sensor 504 of the magnetic induction radio system 500 includes a magnetic loop antenna 508, a transceiver 510 and a measuring unit 512. In the illustrated embodiment of FIG. 10, the magnetic loop antenna 508 is same as the magnetic loop antenna 104 in the embodiment of FIG. 1.

The transceiver 510 of the magnetic induction radio sensor 504 is configured to transmit measurement values of the shape of the object 502 to the remote device 506 using the magnetic loop antenna 508 and to receive commands from the remote device using the magnetic loop antenna. The transceiver includes a medium access control (MAC) time division multiplexing (TDM) scheduler 514, a modulator 516, an amplifier 518, an antenna matching circuit 520, a low noise amplifier (LNA) 522, an RF received signal strength indicator (RSSI) circuit 524, a mixer 526, one or more baseband filters 528, an optional baseband RSSI circuit 530 and a demodulator 532.

The MAC TDM scheduler 514 of the transceiver 510 is configured to repetitively schedule measurement of the shape of the object 502 and transmission of the generated measurement value to the remote device 506 according to predefined slots in a TDM scheme. The MAC TDM scheduler unit may also be configured to schedule the measurement of the shape of the object after reception of a synchronization word from the remote device. Additionally, the MAC TDM scheduler performs frame packing, frame synchronization, frame error detection and frame error correction.

In some embodiments, the MAC TDM scheduler 514 schedules data communications using the magnetic loop antenna 508 and dynamic frequency tuning of the antenna matching circuit 520 according to the TDM scheme to enable sharing or multiplexing of sub-channels on one physical communications channel. The time domain is divided into several recurrent timeslots of a predefined length, where one or more slot is designated to each sub-channel. According to the TDM scheme, to avoid collision, a communications device can use the physical communications channel only when the communications device is aligned or synchronized to a reference time base. In other words, a communications device can use the physical communications channel only when the communications device is assigned at least one time slot for transmission. This reference time base is set by one communications device, which assumes the role of the "master" device. The master device will transmit synchronization sequences in one or more designated time slots and the reference time base is thereby set. Other communications devices in the network with the star topology are also referred to as "slave" devices. For the slave devices to participate in the network, these slave devices must be in the communications range of the master device, listen or receive at least in the time slot, and align their time base with the master device upon hearing from the master device. Although the magnetic induction radio sensor 504 can be the master device, the remote device 506 is usually the master device. Also according to the TDM scheme, there is one random access channel that is shared by the master and slave devices according to a slotted aloha multiplexing scheme.

The basic principle of the slotted aloha multiplexing scheme can be described as follows. If a communications device has no data to send, the communications device listens to all other communications devices. If a communications device has data to send, this communications device sends the data in the first available time slot of the random access channel. If the message that carries the data collides with any other message, this communications device will retry the transmission of the data in a later time slot of the random access channel. Additionally, a slave device that requires a sub-channel can issue a request to the master device using the random access channel. Although communications connections can be established between the slave devices, usually all data communications are from the slave devices to the master device that acts as the data collector. Typically, each magnetic induction radio sensor 504 is assigned one unidirectional sub-channel, in which sensor data is transmitted from the magnetic induction radio sensor to the remote device 506 that serves the master role, and all control messages are exchanged using the random access channel.

The modulator 516 of the transceiver 510 is configured to modulate the signals from the MAC TDM scheduler 514. The amplifier 518 is configured to amplify modulated signals from the modulator. The amplified signals are processed by the antenna matching circuit 520 and transmitted to the remote device 506 through the magnetic loop antenna 508.

Figure 11:
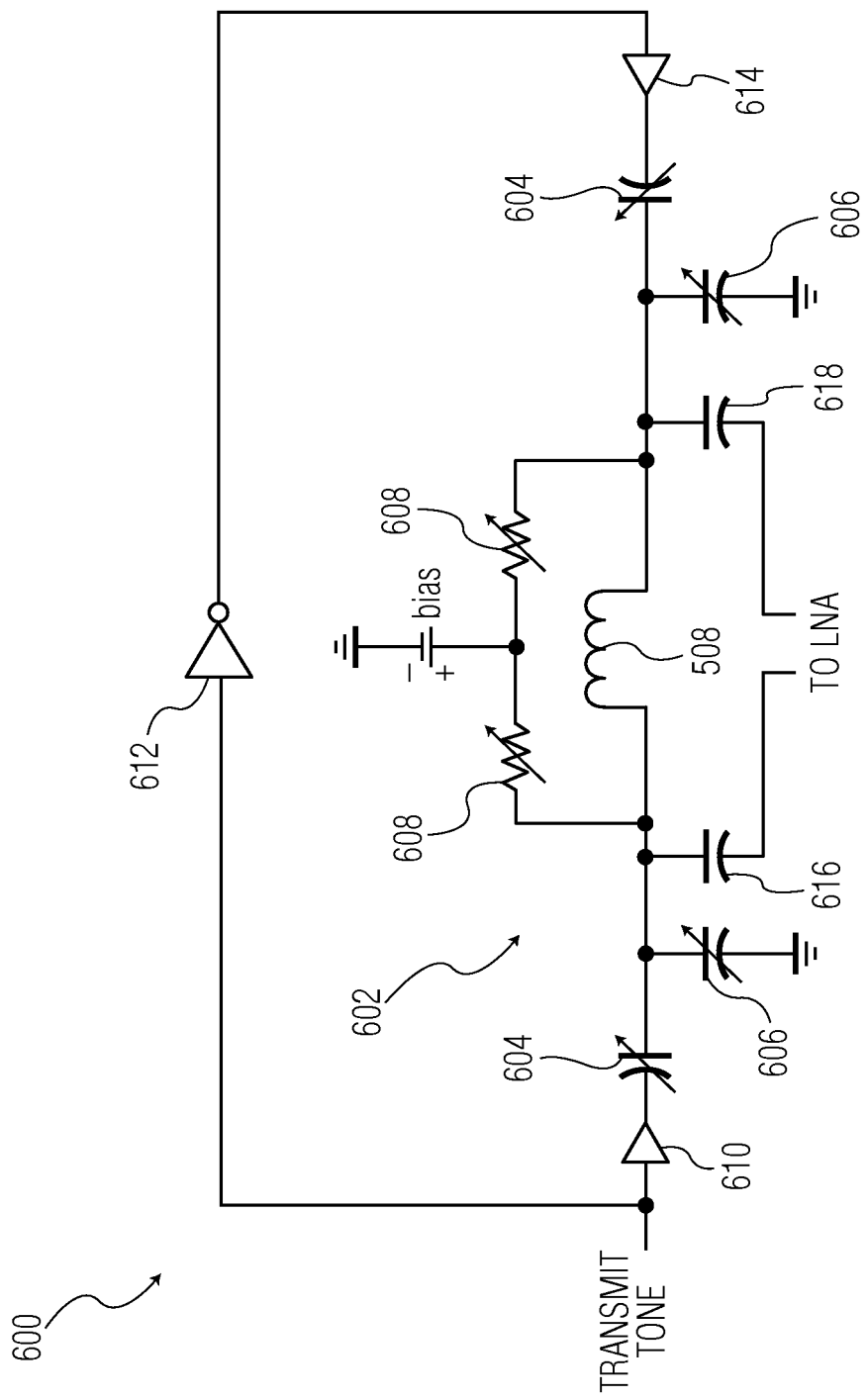
FIG. 11 depicts an exemplary differential input/output stage with an antenna matching circuit.

The antenna matching circuit 520 of the transceiver 510 is coupled to the magnetic loop antenna 508. The antenna matching circuit is configured to provide a particular capacitance such that the magnetic loop antenna and the antenna matching circuit form a resonant circuit 533 and the resonant circuit has a fixed resonant frequency. FIG. 11 depicts an exemplary differential input/output stage 600 of an antenna matching circuit 602. Although the exemplary input/output stage is symmetric for improved signal quality, a single-ended input/output stage can also be used in some embodiments. The antenna matching circuit and the differential input/output stage are separate. As shown in FIG. 11, the antenna matching circuit includes one or more transmission level capacitors 604, one or more tune capacitors 606, and one or more tune resistors 608. The transmission level capacitor and the tune capacitors are variable capacitors. The tune resistors are variable resistors. The transmission level capacitor is connected to the tune capacitor, which is connected to the ground. The tune resistors are coupled to the magnetic loop antenna 508 and a bias voltage source, which is connected to the ground. The transmission level capacitor is used to adjust the transmitted signal level of the magnetic loop antenna. The tune capacitor is used to adjust the resonant frequency of the resonant circuit. The tune capacitor may be the same as the adjustable capacitance module 110 that is described in the embodiments of FIGS. 1, 8 and 9. The tune resistors are used to adjust the equivalent resistance of the antenna matching circuit and the bandwidth of the antenna matching circuit. The differential input/output stage includes a first driver buffer 610, an inverting buffer 612, a second drive buffer 614, and coupling capacitors 616 and 618. The first driver buffer, the inverting buffer and the second buffer together constitute the differential transmitter driver. As shown in FIG. 11, a digital modulated signal "transmit tone" is presented at the first driver buffer, then inverted by the inverting buffer, and finally presented at the second driver buffer. These three buffers are implemented using thick gate oxide transistors for high voltages. Because the transceiver is AC (alternating current) coupled, the coupling capacitors are connected to the magnetic loop antenna and are towards the LNA 522.

Figure 12:
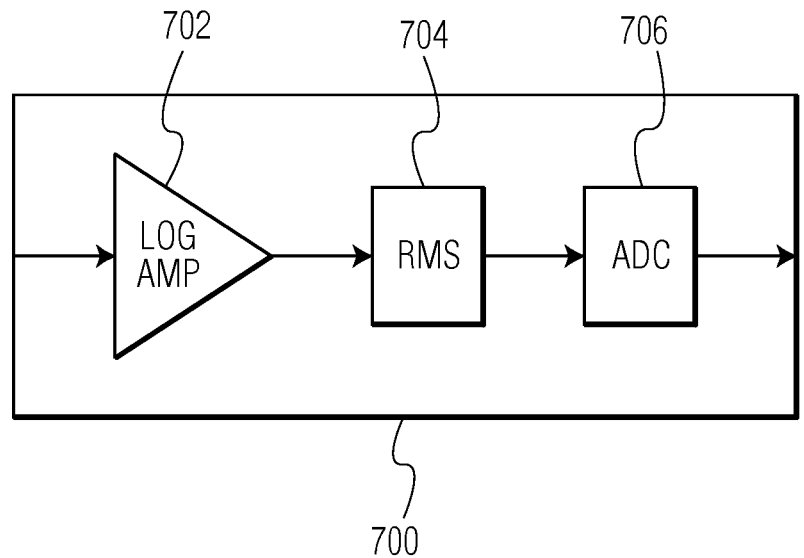
FIG. 12 depicts an exemplary radio frequency received signal strength indicator circuit.

Turning back to FIG. 10, the low noise amplifier (LNA) 522 of the transceiver 510 is configured to amplify received signals. The RF received signal strength indicator (RSSI) circuit 524 is configured to measure the signal strength of the amplified signals. An exemplary RF RSSI circuit 700 is depicted in FIG. 12. In the embodiment of FIG. 12, the RF received signal strength indicator includes a logarithmic amplifier (LOG AMP) 702 for optimal dynamic range, a root mean square (RMS) amplitude detector 704, and an analog-to-digital (ADC) converter 706. The mixer 526 of the transceiver 510 is configured to convert the amplified signals from the LNA 522 in a high carrier frequency to baseband signals in a low baseband frequency. The baseband filter 528 is configured to filter the baseband signals. The optional baseband RSSI circuit 530 is configured to measure the signal strength of the filtered baseband signals. The demodulator 532 is configured to demodulate the filtered baseband signals.

The measuring unit 512 of the magnetic induction radio sensor 504 is configured to generate a measurement value using the capacitance of the antenna matching circuit 520, where the measurement value represents a measurement of the shape of the object 502. The measuring unit includes a dynamic tuning module 534 and a signal conditioning module 536. The dynamic tuning module is configured to tune the capacitance of the antenna matching circuit such that the resonant frequency of the resonant circuit 533 is fixed. For example, the dynamic tuning module tunes the tune capacitor 606 of the antenna matching circuit 602 in the embodiment of FIG. 11 to achieve the fixed resonant frequency when the inductance of the magnetic loop antenna 508 changes. The signal conditioning module is configured to process the capacitance value from the dynamic tuning module to generate measurement data of the shape of the object and to pass the measurement data to the MAC TDM scheduler 514 for transmission.

Figure 13:
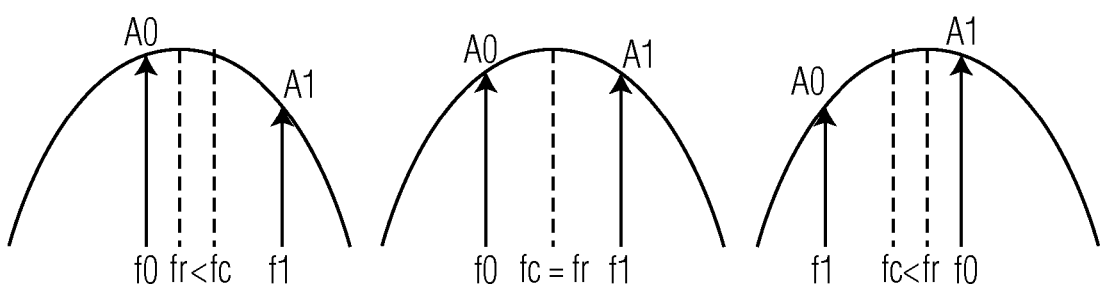
FIG. 13 illustrates three scenarios of alignments of the resonant frequency of an antenna matching circuit and a magnetic loop antenna and with the carrier frequency of a transceiver.

Additionally, the dynamic tuning module 534 can also be used to initially tune the antenna matching circuit 520. In modulation schemes such as frequency shift keying (FSK), logic symbols "0" and "1" are transmitted in different frequencies. However, the logic symbols "0" and "1" may be transmitted and received with different amplitudes due to attenuation in case that the resonant frequency is not aligned to the carrier center frequency for communications. In some embodiment, the transceiver 510 of the magnetic induction radio sensor 504 aligns the resonant frequency of the resonant circuit 533 with the carrier/center frequency of the transceiver such that the logic symbols "0" and "1" are transmitted and received with the same amplitude for optimal transmission and detection. FIG. 13 illustrates three scenarios of alignments of the resonant frequency of the resonant circuit with the carrier/center frequency of the transceiver. The carrier/center frequency $f_c$ is equal to the average of the frequency $f_0$ for transmitting the logic symbol "0" and the frequency $f_1$ for transmitting the logic symbol "1." In other words, $f_c=(f_0+f_1)/2$. As shown in the left side of FIG. 13, the resonant frequency $f_r$ of the resonant circuit is smaller than the carrier/center frequency $f_c$. As shown in the middle of FIG. 13, the resonant frequency $f_r$ of the resonant circuit is equal to the carrier/center frequency $f_c$. As shown in the right side of FIG. 13, the resonant frequency $f_r$ of the resonant circuit is larger than the carrier/center frequency $f_c$. In order to detect frequency misalignment, the magnetic induction radio sensor transmits the logic symbols in frequency bands $f_0$ and $f_1$ and detects the signal amplitudes $A_0$ and $A_1$ through the received signal in the RF RSSI circuit 524. If $A_0>A_1$ and $f_r<f_c$, the resonant frequency $f_r$ should be increased for proper alignment. In this case, the dynamic tuning module reduces the capacitance of the tune capacitor 606. If $A_0<A_1$ and $f_r>f_c$, the resonant frequency $f_r$ should be decreased for proper alignment. In this case, the dynamic tuning module increases the capacitance of the tune capacitor.

Additionally, to avoid having the signal strength measurement interfered by other devices, the tuning of the magnetic induction radio sensor 504 is scheduled in a free time slot. Because the transmission power level of the tuning is low, all of the communications devices can perform the tuning simultaneously in the same time slot. A designated slot can be assigned using a portion of the total network bandwidth. Alternatively, a designated slot can be assigned without using network bandwidth. In an example, the random access channel is often free, which is intrinsic to the slotted aloha scheme. In another example, each data packet can be preceded by a synchronization sequence for data alignment purposes. For a communications device to receive a data packet, the communications device must detect the synchronization sequence of the data packet within a limited time window. When no communications device is transmitting and every communications device is listening to the communications channel, all of the communications devices will fail to receive the synchronization sequence within the limited time window. As a result, all of the communications devices can use the remainder of the time slot for tuning.

In some embodiments, the magnetic induction radio sensor 504 includes a rechargeable battery (not shown) and an inductive charging circuit (not shown). The rechargeable battery is charged when the magnetic loop antenna 508 is placed in a magnetic field generated by the inductive charging circuit. The inductive charging circuit may further serve as a read out device for the magnetic induction radio sensor. Alternatively, the magnetic loop antenna may be further configured to receive direct inductive power such that the magnetic induction radio sensor is configured to operate without any battery using the received direct inductive power.

The remote device 506 of the magnetic induction radio system 500 includes an antenna 538, a receiver/transmitter 540 that is also referred to as a transceiver, a processor 542 and an optional display 544. The antenna of the remote device may be a conventional loop antenna, a spiral flat printed circuit board (PCB) antenna or a solenoid with or without a ferrite core. The transceiver 540 of the remote device 506 may be similar or identical to the transceiver 510 of the magnetic induction radio sensor 504. The processor of the remote device may be any type of a controller or a processor, such as a digital signal processor or an application-specific processor. The optional display of the remote device may be any type of a display, such as a personal computer monitor.

Figure 14:
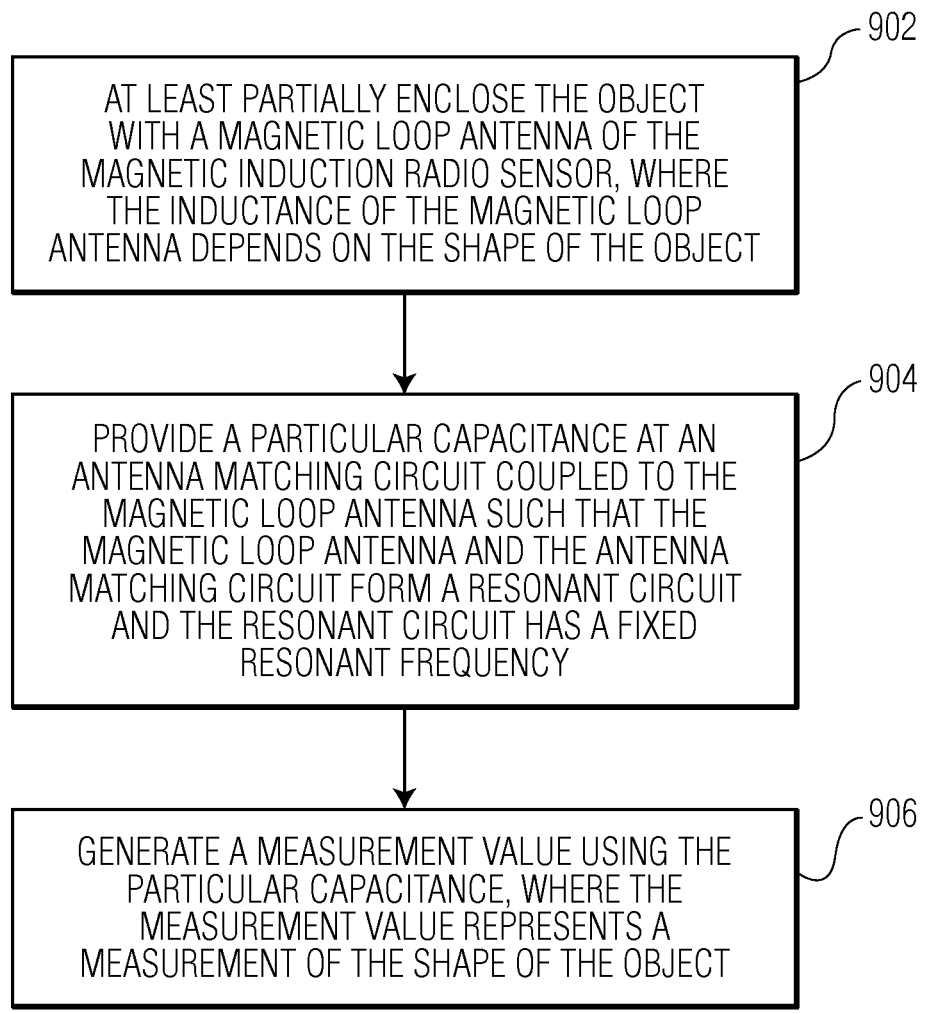
FIG. 14 is a process flow diagram of a method for measuring the shape of an object using a magnetic induction radio sensor in accordance with an embodiment of the invention.

FIG. 14 is a process flow diagram of a method for measuring the shape of an object using a magnetic induction radio sensor in accordance with an embodiment of the invention. At block 902, the object is at least partially enclosed using a magnetic loop antenna, where the inductance of the magnetic loop antenna depends on the shape of the object. At block 904, a particular capacitance is provided at an antenna matching circuit coupled to the magnetic loop antenna such that the magnetic loop antenna and the antenna matching circuit form a resonant circuit and the resonant circuit has a fixed resonant frequency. At block 906, a measurement value is generated using the particular capacitance, where the measurement value represents a measurement of the shape of the object.

Embodiments of the invention can be used for medical, health and fitness applications. For example, embodiments of the invention can be used for inductance plethysmography, i.e., measurement of expansion and/or contraction of body parts, such as lungs in respiratory inductance plethysmography (RIP), limbs that include arms and legs, and in penile plethysmography. Embodiments of the invention can also be used in baby monitors for sudden infant death prevention, breathing aids, stress monitoring and sports monitoring during exercising. Additionally, embodiments of the invention can be easily integrated with measurement of bio-potentials at the enclosed body part to providing combinations of Electromyography (EMG) with muscle expansion, and Electrocardiography (ECG) with respiration.

Although the operations of the method herein are shown and described in a particular order, the order of the operations of the method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

In addition, although specific embodiments of the invention that have been described or depicted include several components described or depicted herein, other embodiments of the invention may include fewer or more components to implement less or more functionality.

Furthermore, although specific embodiments of the invention have been described and depicted, the invention is not to be limited to the specific forms or arrangements of parts so described and depicted. The scope of the invention is to be defined by the claims appended hereto and their equivalents.

What is claimed is:

1. A magnetic induction radio sensor configured for measuring the shape of an object, the magnetic induction radio sensor comprising:
    a magnetic loop antenna configured to at least partially enclose the object, wherein the inductance of the magnetic loop antenna depends on the shape of the object, wherein the magnetic loop antenna is configured to deform as a result of expansion and/or contraction of the object;
    an antenna matching circuit coupled to the magnetic loop antenna, wherein the antenna matching circuit comprises an adjustable capacitance module configured to provide a particular capacitance such that the magnetic loop antenna and the antenna matching circuit form a resonant circuit and the resonant circuit has a fixed resonant frequency; and
    a measuring unit configured to generate a measurement value using the particular capacitance of the adjustable capacitance module, the measurement value representing a measurement of the shape of the object,
    wherein the object is an organ of a patient, and wherein the magnetic loop antenna is integrated in a stretchable strap that at least partially encloses the organ of the patient.

2. The magnetic induction radio sensor of claim 1, wherein the adjustable capacitance module comprises an array of switchable capacitors in order to provide the particular capacitance.

3. The magnetic induction radio sensor of claim 2, wherein the array of switchable capacitors comprises capacitor branches that are connected in parallel with the magnetic loop antenna, and wherein each of the capacitor branches comprises a switch and a capacitor.

4. The magnetic induction radio sensor of claim 3, wherein capacitances of the capacitors in the capacitor branches have a numeric relationship of factors of two.

5. The magnetic induction radio sensor of claim 2, wherein capacitances of the capacitors in the capacitor branches are equal.

6. The magnetic induction radio sensor of claim 1, comprising multiple magnetic loop antennas configured to at least partially enclose the object, wherein the inductances of the magnetic loop antennas depend on the shape of the object, the magnetic induction radio sensor further comprising an array of switches configured for selecting the magnetic loop antennas.

7. The magnetic induction radio sensor of claim 1 further comprising a transmitter configured to transmit the generated measurement value to a remote device using the magnetic loop antenna.

8. The magnetic induction radio sensor of claim 7 further comprising a scheduling unit configured to repetitively schedule measurement of the shape of the object and transmission of the generated measurement value to the remote device according to predefined slots in a time division multiplexing scheme.

9. The magnetic induction radio sensor of claim 8, wherein the scheduling unit is further configured to schedule the measurement of the shape of the object after reception of a synchronization word from the remote device.

10. The magnetic induction radio sensor of claim 1 further comprising:
   an inductive charging circuit; and
   a rechargeable battery, wherein the rechargeable battery is charged when the magnetic loop antenna is placed in a magnetic field generated by the inductive charging circuit;
   or the magnetic loop antenna is further configured to receive direct inductive power such that the magnetic induction radio sensor of claim 1 is configured to operate without a battery using the received direct inductive power.

11. The magnetic induction radio sensor of claim 1 further comprising contact electrodes integrated in the stretchable strap and configured to measure bio-potentials of the patient.

12. The magnetic induction radio sensor of claim 11, wherein the organ is a lung of the patient, and wherein the stretchable strap wraps around the chest and/or abdomen of the patient in order to measure expansion and/or contraction of the torso of the patient to measure respiration of the patient.

13. The magnetic induction radio sensor of claim 11, wherein the organ is a limb of the patient, and wherein the stretchable strap wraps around the limb of the patient in order to measure expansion and/or contraction of muscles of the limb.

14. A method of measuring the shape of an object using a magnetic induction radio sensor, the method comprising:
   at least partially enclosing the object with a magnetic loop antenna of the magnetic induction radio sensor, wherein the inductance of the magnetic loop antenna depends on the shape of the object;
   providing a particular capacitance at an antenna matching circuit coupled to the magnetic loop antenna such that the magnetic loop antenna and the antenna matching circuit form a resonant circuit and the resonant circuit has a fixed resonant frequency; and
   generating a measurement value using the particular capacitance, the measurement value representing a measurement of the shape of the object,
   wherein the object is an organ of a patient and wherein the magnetic loop antenna is integrated in a stretchable strap that at least partially encloses the organ of the patient.

15. The method of claim 14 further comprising adjusting the particular capacitance in response to a deformation of the magnetic loop antenna as a result of expansion and/or contraction of the object such that the resonant circuit still has the fixed resonant frequency.

16. The method of claim 15, wherein the providing the particular capacitance comprises providing the particular capacitance using an array of switchable capacitors, wherein the array of switchable capacitors comprises capacitor branches that are connected in parallel with the magnetic loop antenna, and wherein each of the capacitor branches comprises a switch and a capacitor.

17. A magnetic induction radio system configured for measuring the shape of an object, the magnetic induction radio system comprising:
   a magnetic induction radio sensor comprising:
      a magnetic loop antenna configured to at least partially enclose the object, wherein the inductance of the magnetic loop antenna depends on the shape of the object;
      an antenna matching circuit coupled to the magnetic loop antenna, wherein the antenna matching circuit comprises an adjustable capacitance module configured to provide a particular capacitance such that the magnetic loop antenna and the antenna matching circuit form a resonant circuit and the resonant circuit has a fixed resonant frequency;
      a measuring unit configured to generate a measurement value using the particular capacitance of the adjustable capacitance module, the measurement value representing a measurement of the shape of the object; and
      a transmitter configured to transmit the generated measurement value using the magnetic loop antenna; and
   a remote device configured to receive the transmitted measurement value from the transmitter of the magnetic induction radio sensor,
   wherein the object is an organ of a patient and wherein the magnetic loop antenna is integrated in a stretchable strap that at least partially encloses the organ of the patient.

18. The magnetic induction radio system of claim 17, wherein the adjustable capacitance module comprises an array of switchable capacitors in order to provide the particular capacitance.

* * * * *